United States Patent [19]

Nickell

[11] 3,930,840
[45] Jan. 6, 1976

[54] RIPENING OF SUGARCANE BY USE OF CERTAIN ALCOHOLIC AND ETHOXYLATED COMPOUNDS

[75] Inventor: Louis G. Nickell, Honolulu, Hawaii

[73] Assignee: Hawaiian Sugar Planters' Association, Honolulu, Hawaii

[22] Filed: Apr. 5, 1974

[21] Appl. No.: 458,459

Related U.S. Application Data

[63] Continuation-in-part of Ser. No. 112,470, Feb. 3, 1971, abandoned.

[52] U.S. Cl. .................................................. 71/122
[51] Int. Cl.² .......................................... A01N 9/24
[58] Field of Search ...................................... 71/122

[56] References Cited
UNITED STATES PATENTS

| | | | |
|---|---|---|---|
| 3,224,865 | 12/1965 | Carlson | 71/115 |
| 3,630,717 | 12/1971 | Miller | 71/122 |
| 3,672,865 | 6/1972 | Ellis | 71/106 |

OTHER PUBLICATIONS

Romaiah et al., Proceedings, 29th Annual Convention of the Sugar Tech. Assoc. of India, 1961, Part II.

*Primary Examiner*—Lewis Gotts
*Assistant Examiner*—Catherine L. Mills
*Attorney, Agent, or Firm*—Burns, Doane, Swecker & Mathis

[57] ABSTRACT

Sucrose yield of sugarcane is increased by treating sugarcane a few weeks prior to harvest with a ripening agent which is composed essentially of a compound selected from the group consisting of linear alcohols containing from 11 to 15 carbon atoms, polyalkylene glycols and ethoxylated compounds of the general formula

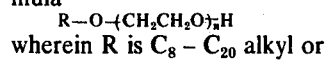

wherein R is $C_8 - C_{20}$ alkyl or

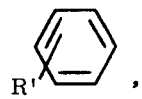

R' being hydrogen or alkyl of 8 to 15 carbon atoms, and $n$ is an integer from 6 to 20, in an amount sufficient to increase sucrose yield.

13 Claims, No Drawings

RIPENING OF SUGARCANE BY USE OF CERTAIN ALCOHOLIC AND ETHOXYLATED COMPOUNDS

REFERENCE TO RELATED APPLICATIONS

This application is a continuation-in-part of copending application Ser. No. 112,470, filed Feb. 3, 1971 and now abandoned.

BACKGROUND OF THE INVENTION

Considerable progress has been made in the last several years in increasing the sugar yield by improving the varieties being planted, enriching the soil with fertilizers and irrigating the soil in climates which do not naturally provide sufficient moisture for optimum plant growth. More recent efforts in improving sugar production have increasingly turned toward the use of chemicals in modifying and controlling the physiological processes of sugarcane, particularly in ripening prior to harvest. See U.S. Pat. Nos. 3,224,865; 3,245,775; 3,291,592; 3,482,958; 3,482,959; 3,492,961; and 3,493,361.

With some compounds previously suggested for this purpose there has been some concern about their resistance to breakdown in the plant and their persistence in the soil when the intended use of the sugar is nutritive as opposed to industrial (e.g., in fermentation processes). Consequently, extensive efforts continue to be made in searching for physiologically harmless or rapidly degradable chemical agents that can be effectively used to modify the ripening of sugarcane so as to increase the sucrose yield therefrom.

Generally speaking, chemicals selected for evaluation have been of types which have been previously found active in work with other plants as plant hormones, herbicides or inhibitors of growth of terminal buds, or active in killing the spindle of cane upon topical micro-application, etc. However, among the compounds heretofore found to be useful for such other special purposes, very few have been found effective in controlling the ripening of sugarcane in the desirable manner. No relationship has been recognized to date between the chemical structure of such compounds and (a) their phytotoxic effects, (b) their physiological effects on the morphogenetic development of the plant, and (c) their activity in having positive effects on ripening. In other words, the effectiveness of a compound in controlling the ripening of sugarcane and thereby increasing sugar yield remains essentially unpredictable, and the search for suitable agents continues to be fundamentally empirical.

A review of the literature discloses that some work has been done using surfactants to increase the crystallization rate of cane sugar and in the purification of sugar juices. See Ramaiah et al, Proceedings, 29th Annual Convention of the Sugar Tech. Assoc. of India, 1961, Part II. Some of the surfactant compounds of the present invention have also been used in very minor, i.e., surfactant, amounts simply as wetting agents in applying an active ingredient such as a benzoic acid compound to cane stalks for sugarcane ripening. See, for example, U.S. Pat. No. 3,224,865 wherein ethoxylated alcohol surfactants are used as wetting agents. However, surfactants produced by the ethoxylation of phenols or higher alcohols have not been recognized as useful per se as sugarcane ripening agents. Ethoxylated phenol and higher alcohol nonionic surfactants are available commercially, and are regarded as materials of only slight to moderate oral and skin penetration toxicity. Such compounds have been exempted by the Food and Drug Administration from tolerance requirements when used in or on raw agricultural commodities (see Federal Register, Vol. 35, No. 161, Aug. 19, 1970).

It is an object of this invention to provide new agents for controlling the ripening of sugarcane. A more specific object is to increase the sucrose yield of sugarcane by chemically treating it during its final ripening stages prior to harvest without introducing substantial toxicological hazards, and preferably without causing visible (phytotoxic) damage to the cane plant, such as drying of the spindle or other leaf.

Still more specifically, it is an object of this invention to increase the sucrose yield of sugarcane by treating it prior to harvest with a chemical agent which is sufficiently stable to provide the desired effect over a period of several weeks and thus give adequate operational flexibility, but which has a relatively low degree of persistence in the soil and is susceptible to decomposition by soil bacteria.

SUMMARY OF THE INVENTION

It has now been discovered that excellent results in increasing the sucrose yield of sugarcane can be obtained by treating the younger, growing parts of the cane stalk a few weeks before harvest with a compound selected from the group consisting of linear alcohols containing from 11 to 15 carbon atoms, polyalkylene glycols and ethoxylated phenols or aliphatic alcohols containing from about 6 to about 20 ethoxy groups, or mixtures thereof and in an amount sufficient to increase sucrose yield. In the two last mentioned classes of compounds, the phenol moiety of such a compound may be substituted by a higher alkyl group; the aliphatic alcohol moiety of such a compound should contain from 8 to 20 carbon atoms. The preferred usage form in this invention is an aqueous solution or suspension containing the active compound as the sole active ripening agent.

A great number of compounds are known to be useful as surfactants for various types of active ingredients including herbicides, pesticides, plant growth regulants, plant hormones and sugarcane ripening agents. Many of these known surfactant compounds have been tested for sugarcane ripening abilities without success. Although the above-defined compounds are among those compounds generally known as surfactants and at least some of them have been used or suggested for use as a surfactant in an aqueous composition containing a recognized sugarcane ripening agent, it has surprisingly been found that the particular compounds defined above are themselves as sugarcane ripening agents when applied to field growing sugarcane as the sole active component and in an amount sufficient to increase sucrose yield.

The linear alcohols which have been found to be effective as ripening agents herein are those containing 11 to 15 carbon atoms. Exemplary compounds are undecyl alcohol, dodecyl alcohol, tridecyl alcohol, tetradecyl alcohol and pentadecyl alcohol.

The effective polyalkylene glycols are those wherein the repeating oxyalkylene group contains from 2 to 3 carbon atoms and wherein the molecular weight is from about 2000 to about 4000. Examples are polyethylene glycol and polypropylene glycol.

The ethoxylated phenols and aliphatic alcohols useful herein correspond to the formula $$R-O+CH_2CH_2O)_nH$$

wherein R is selected from the group consisting of phenyl groups which may be substituted with an alkyl group of 8 to 15 carbon atoms, and alkyl groups containing from 8 to 20 carbon atoms, and $n$ is an integer from about 6 to about 20.

Exemplary of the phenols and aliphatic alcohols which may be ethoxylated to form the compounds suitable for use in the invention include: phenol, nonylphenol, dodecylphenol, cetylphenol, octadecyl phenol, nonanol, trimethylnonanol, undecanol, dodecanol, tetradecanol, pentadecanol, cetyl alcohol, and octadecanol. The alcohols may have a straight chain or a branched chain, e.g., they may be of the type resulting from the oxo process.

The polyethoxy group may be of moderate size, containing from about 6 to about 20 ethoxy groups.

Specific examples of suitable ethoxylated phenolic and alcoholic compounds are α-(p-nonylphenyl)-ω-hydroxypoly(oxyethylene) wherein the poly(oxyethylene) content averages 10.5 moles, α-(undecyl)-ω-hydroxy-poly(oxyethylene) wherein the poly(oxyethylene) content averages 3-12 moles, α-(tridecyl)-ω-hydroxypoly(oxyethylene) wherein the poly(oxyethylene) content averages 3-12 moles, and α-(pentadecyl)-ω-hydroxypoly(oxyethylene) wherein the poly(oxyethylene) content averages 3-12 moles.

Among the ethoxylated compounds, the linear alcohol ethoxylates exhibit significantly increased biodegradability over previously available nonionic surfactants, such as alkylphenol derived materials.

In accordance with this invention the sugarcane crop is treated with the linear alcohol, polyalkylene glycol, or ethoxylated phenol or aliphatic alcohol, or with a composition containing one or more of such compounds as its sole active ingredient, at any time from 2 to 12 weeks before harvest, the preferred time for treatment being between about 3 to 8 weeks prior to harvest.

The sugarcane crop is treated with the above-defined active compounds in an amount sufficient to increase the sucrose yield obtained from the sugarcane. Excellent results are obtained when the sugarcane crop is treated at a rate in the range of from about 3 to about 4 pounds up to about 10 pounds or more, for example, up to about 40 or 60 pounds per acre or more of the active compound per acre of sugarcane, though higher rates may be used. The optimum amount will vary somewhat depending on the specific treating composition applied, environmental conditions, time of year, age of cane and in some cases the specific variety of cane being treated, but can be readily determined for each particular case by preliminary testing. It has been found that amounts of less than about 1 pound of the compound per acre are ineffective for increasing the sucrose yield of the growing sugarcane.

Although the ethoxylated compounds are effective both in anionic and nonionic forms, the latter is preferred because of ease in handling and storage (the anionic compounds are presently available commercially only in highly corrosive solutions).

The active agent is conveniently applied in the field in the form of an aqueous solution or suspension, e.g., a liquid composition which may be sprayed from a boom-spray or a solid dust composition where the active compound is diluted with an inert solid such as clay and when can be applied as a dust from an airplane.

With the type of boom-spray apparatus used in this work, it has been found convenient to apply the active compound to the sugarcane field in the form of an aqueous solution, suspension, or emulsion having a concentration of active agent such that the application at the rate of from 7 to 20 gallons of liquid composition per acre will provide the required dosage of active chemical. However, the use of lower or higher gallonages may be preferred when a different dispensing mechanism is used.

Water is the preferred liquid carrier for the active ripeners in practicing the present invention. Most of the compounds of interest are liquids under normal ambient conditions, though the solid species falling within the scope of the present invention are similarly useful. Instead of using water as the carrier, non-phytotoxic mineral oils either as such or in the form of water-in-oil or oil-in-water emulsions may be used similarly in accordance with practices which are common in the art of treating vegetation with beneficial growth control agents. Other active ingredients are not required and are preferably omitted.

DESCRIPTION OF SPECIFIC EMBODIMENTS

EXAMPLE I

The compound applied to the cane stalks was a mixture of linear alcohols containing 11 to 15 carbon atoms which had been ethoxylated so that the average number of ethoxy groups was about 7. 0.3 ml. of the mixture of linear alcohol ethoxylates (15-LAE-7) in 50 percent aqueous solution was deposited or dropped by means of a syringe with a fine needle on the spindle area at the top or last visible dewlap of each of 20 stalks of sufarcane 16 months of age. 0.3 ml/stalk corresponds to a rate of about 33 lb/acre. (A dewlap is the junction between the blade of the leaf and the sheath which clasps the stalk.) Ten of these stalks were harvested 4 weeks after such treatment and ten more were harvested 5 weeks after such treatment. An equal number of stalks of the same age were treated in an identical manner with a mixture of the same kind of linear alcohol ethoxylates wherein the average number of ethoxy groups was 9 (15-LAE-9).

"Trysben" (dimethylamine salt of trichlorobenzoic acid), a known sugarcane ripening agent, was also used to treat an equal number of stalks for comparison purposes because of its consistent activity. The Trysben commercial product (a 50 weight percent aqueous solution of the salt available from the E. I. duPont de Nemours and Co.) was diluted with an equal weight of water and the resulting solution (which also contains about 0.25 weight percent nonylphenyl ethoxylated to contain about 10.5 moles of ethylene oxide per mole of nonylphenyl) was applied to the stalks in the manner described above in an amount of 0.3 ml/stalk which is equivalent to 4 lbs/acre of Trysben.

The top 15 joints of the treated cane as well as those of similar untreated cane were removed and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. Determination of the pol percent cane is a standard and effective method for determining the sucrose content of sugarcane. The results are given below:

|  | Time of Harvest | | | |
|---|---|---|---|---|
|  | Four Weeks After Application | | Five Weeks After Application | |
|  | Juice Purity | Pol % Cane | Juice Purity | Pol % Cane |
| Control (untreated) | 59.52 | 5.71 | 67.68 | 6.93 |
| Trysben (standard) (4 lbs/acre) | 69.58 | 8.00 | 69.70 | 7.81 |
| 15-LAE-7 (33 lbs/acre) | 68.48 | 7.94 | 79.18 | 9.44 |
| 15-LAE-9 (33 lbs/acre) | 73.63 | 8.40 | 73.39 | 8.59 |

As is apparent, the application of the compounds of the invention resulted in a very substantial improvement in both juice purity and pol percent cane.

EXAMPLE II

The procedure of Example I was repeated on the stalks of cane 19.5 months of age using compounds comprising a mixture of the same linear alcohol ethoxylates, except that an equal number of stalks were treated with compounds wherein the average number of ethoxy groups was three (15-LAE-3), five (15-LAE-5), and twelve (15-LAE-12). The following results were obtained:

|  | Time of Harvest | | | |
|---|---|---|---|---|
|  | Four Weeks After Application | | Five Weeks After Application | |
|  | Juice Purity | Pol % Cane | Juice Purity | Pol % Cane |
| Control (untreated) | 70.64 | 7.95 | 67.96 | 7.61 |
| Trysben (standard) (4 lbs/acre) | 76.12 | 9.10 | 72.19 | 8.93 |
| 15-LAE-3 (33 lbs/acre) | 61.76 | 5.99 | 55.46 | 5.54 |
| 15-LAE-5 (33 lbs/acre) | 71.83 | 7.92 | 65.30 | 6.96 |
| 15-LAE-12 (33 lbs/acre) | 78.11 | 10.42 | 75.92 | 11.00 |

The results again show a distinct improvement in both sucrose yield and juice purity resulting from treating the cane with a compound of the invention, 15-LAE-12. On the other hand, the other two ethoxylated alcohols, 15-LAE-3 and 15-LAE-5, which are chemically similar to 15-LAE-12 except for their lower degree of ethoxylation, have been found to be essentially ineffective as ripeners.

EXAMPLE III

The procedure of Example I was repeated on stalks 20.2 months of age using alkyl phenyl ethoxylate (APE) wherein the alkyl group contains 9 carbon atoms and the average number of ethoxy groups per mole was 10.5 (9APE-10.5). An equal number of the same stalks were treated with the same compound using twice as much as in Example I or 0.6 ml/stalk (which corresponds to a rate of 66 lb/acre). The following results were obtained:

|  | Time of Harvest | | | |
|---|---|---|---|---|
|  | Four Weeks After Application | | Five Weeks After Application | |
|  | Juice Purity | Pol % Cane | Juice Purity | Pol % Cane |
| Control (untreated) | 79.01 | 9.59 | 81.39 | 10.61 |
| Trysben (standard) (4 lbs/acre) | 82.38 | 11.48 | 82.88 | 11.99 |
| 9-APE-10.5 (33 lbs/acre) | 86.37 | 13.38 | 86.72 | 13.39 |
| 9-APE-10.5 (66 lbs/acre) | 83.91 | 12.74 | 85.04 | 12.95 |

A very apparent improvement in sucrose yield and juice purity again result from the use of the invention. Furthermore, the results of Examples I, II, and III indicate that compounds of the invention are highly effective for the intended purpose relatively independently of the degree of ripeness which the cane has naturally reached at the time of treatment, and relatively independently of the amount of agent applied. As can be seen, 0.3 ml of active compound per stalk is ample to produce the desired effect, but a higher dosage produces no further benefits.

EXAMPLE IV

The procedure of Example I was repeated on stalks 20.0 months of age using phenyl ethoxylate wherein the average number of ethoxy groups per mole is 15 (PE-15), nonylphenyl ethoxylate wherein the average number of ethoxy groups per mole is 7 (9-APE-7), nonylphenyl ethoxylate wherein the average number of ethoxy groups per mole is 9 (9-APE-9), nonylphenyl ethoxylate wherein the average number of ethoxy groups per mole is 15 (9-APE-15), and dodecylphenyl ethoxylate wherein the average number of ethoxy groups per mole is 6 (12-APE-6). The results are shown below:

|  | Time of Harvest | | | |
|---|---|---|---|---|
|  | Four Weeks After Application | | Five Weeks After Application | |
|  | Juice Purity | Pol % Cane | Juice Purity | Pol % Cane |
| Control (untreated) | 63.64 | 6.55 | 70.81 | 7.95 |
| Trysben (standard) (4 lbs/acre) | 81.10 | 10.65 | 77.34 | 9.94 |
| PE-15 (33 lbs/acre) | 77.22 | 9.69 | 78.45 | 10.77 |
| 9-APE-7 (33 lbs/acre) | 75.19 | 9.49 | 67.68 | 7.42 |
| 9-APE-9 (33 lbs/acre) | 77.55 | 9.57 | 70.80 | 8.51 |
| 9-APE-15 (33 lbs/acre) | 76.43 | 9.54 | 76.33 | 10.10 |
| 12-APE-6 (33 lbs/acre) | 59.85 | 5.80 | 76.90 | 10.03 |

The essentially empirical nature of the present invention is demonstrated in the results in that nonylphenyl ethoxylate wherein the average number of ethoxy groups is 7 (9-APE-7) was very effective if cane treated with it was harvested within four weeks after application but was essentially ineffective when harvest was delayed unitl the fifth week. Conversely, dodecylphenyl ethoxylate wherein the average number of ethoxy groups per molecule is 6 (12-APE-6) was very effective if applied five weeks before harvest but was not noticeably effective when cane treated with it was harvested only four weeks after treatment.

EXAMPLE V

The procedure of Example I was repeated on stalks 20.0 months of age using trimethylnonanyl ethoxylate wherein the average number of ethoxy groups per mole is 6 (TMN-6) and a mixture of $C_{14}$ to $C_{15}$ linear alcohol ethoxylates wherein the average number of ethoxy groups per mole is 10 (45-LAE-10). Also applied were a mixture of $C_{11}$ to $C_{15}$ linear alcohols (15-LA) and polyethylene glycol (PEG) of approximately 2500 molecular weight. The results are shown below:

| | Time of Harvest | | | |
|---|---|---|---|---|
| | Four Weeks After Application | | Five Weeks After Application | |
| | Juice Purity | Pol % Cane | Juice Purity | Pol % Cane |
| Control (untreated) | 63.64 | 6.55 | 70.81 | 7.95 |
| Trysben (standard) (4 lbs/acre) | 81.10 | 10.65 | 77.34 | 9.94 |
| TMN-6 (33 lbs/acre) | 62.35 | 7.12 | 76.30 | 10.29 |
| 45-LAE-10 (33 lbs/acre) | 73.10 | 8.54 | 83.58 | 12.18 |
| 15-LA (33 lbs/acre) | 70.63 | 9.05 | 82.65 | 11.70 |
| PEG(33 lbs/acre) | 77.35 | 9.84 | 74.96 | 9.55 |

Again the excellent results obtainable when using compounds of the invention are observable.

COMPARATIVE EXAMPLE A

A number of compounds which are known and used as surfactants in various applications were tested in the same manner as the compounds of the present invention. Among the compounds tested were "Aerosol OT" (dioctyl ester of sodium sulfosuccinic acid) which showed little or no sugarcane ripening activity and a large group of substituted benzene sulfonic acids, benzene sulfonamides, benzene sulfinic acids, phenyl sulfones and benzyl sulfones, none of which showed any sugarcane ripening activity. Representative runs utilizing these compounds are given below in Table A.

Table A

| | Time of Harvest | | | |
|---|---|---|---|---|
| | Four Weeks After Application | | Five Weeks After Application | |
| Compound | Juice Purity | Pol % Cane | Juice Purity | Pol % Cane |
| Aerosol OT[1] | 66.49 | 8.88 | 65.17 | 6.72 |
| Control | 64.40 | 6.72 | 68.42 | 7.56 |
| 3,3'-dinitro-4,4'-dichloro-diphenylsulfone[2] | 63.88 | 7.05 | 65.47 | 6.44 |
| Control | 63.93 | 6.81 | 71.68 | 7.98 |
| 2,4,5-trichlorophenyl-benzylsulfone[2] | 51.29 | 3.86 | 57.33 | 4.99 |
| Control | 56.53 | 5.16 | 63.59 | 6.17 |

[1] Applied to growing sugarcane, 20.25 months of age, at a rate of 0.3 ml/stalk which corresponds to 33 lb/acre.
[2] Applied to growing sugarcane, 22 months of age, at a rate of 38 ml/stalk which corresponds to 4 lb/acre.

Other known surfactants which are tested on field grown sugarcane with similar results include 2,4-dinitrobenzene sulfonic acid; N'-n-butyl-3-amino-4-methoxybenzene-sulfonamide; N-diethyl-3-amino-4-methoxy-benzene-sulfonamide; 3,4,3',4'-tetrachlorodiphenylsulfone; 2,4,5-trichlorobenzene sulfinate; 2,4,5-trichlorophenylsulfone; 2,4-dinitro-4'-chlorodiphenylsulfone; 4-nitro-2,4'-dichlorodiphenylsulfone; 3,4,4'-trichlorodiphenylsulfone; 2,4,4',5-tetrachlorodiphenylsulfone; 5-nitro-1',4',5'-trichlorodiphenylsulfone; 2-chloro-4-nitrodiphenylsulfone; p-chlorophenylbenzyl sulfone; 2-chloro-4-nitrophenylbenzylsulfone; and butyl methane sulfonate.

These results show that the use of a particular material as a surfactant has no relationship to the activity (or lack thereof) of the same material as a sugarcane ripening agent.

COMPARATIVE EXAMPLE B

Field growing sugarcane is contacted with an aqueous composition of an experimental active ripener and 0.05 lb/acre of a surfactant of the compound of Example III (9-APE-10.5). A similar area is treated with an aqueous composition of the same experimental active ripener without the surfactant. Samples are taken from each area each week for 13 weeks after application and the purity and pol percent cane are determined. The results are shown below in Table B.

Table B

| Weeks after application | Purity With | Without | (Difference) | Pol % Cane With | Without | (Difference) |
|---|---|---|---|---|---|---|
| 0 | 75.7 | 73.2 | + | 8.3 | 7.9 | = |
| 1 | 76.7 | 79.9 | – | 8.7 | 9.5 | – |
| 2 | 78.4 | 78.5 | = | 9.2 | 9.1 | = |
| 3 | 71.6 | 74.9 | – | 7.8 | 8.4 | – |
| 4 | 72.0 | 69.6 | + | 7.9 | 7.1 | + |
| 5 | 74.8 | 73.4 | = | 9.1 | 8.0 | + |
| 6 | 73.7 | 74.5 | = | 8.7 | 8.2 | = |
| 7 | 75.3 | 76.7 | = | 9.0 | 9.2 | = |
| 8 | 77.9 | 81.4 | – | 9.8 | 10.7 | – |
| 9 | 78.7 | 73.5 | + | 10.3 | 8.5 | + |
| 10 | 79.5 | 76.4 | + | 10.9 | 10.1 | + |
| 11 | 82.2 | 81.8 | = | 10.9 | 10.5 | = |
| 12 | 80.8 | 82.2 | = | 11.1 | 11.3 | = |
| 13 | 78.3 | 79.7 | = | 10.5 | 10.7 | = |

If it is assumed in this instance that it takes at least 2 points of purity to make a significant difference, then there were 4 gains, 3 losses, and 7 evens for the 13 weeks of sampling. Further, if it is assumed that at least one-half point of pol percent cane is enough to make a significant difference, then there were 4 gains, 3 losses, and 6 evens for 13 weeks of sampling. All of which strongly indicates that there is no effect whatsoever of surface active agents added at this level, 0.05 lb/acre, a commonly used level of surfactant for this type of application.

COMPARATIVE EXAMPLE C

The compound of Example III (9-APE-10.5) was applied to field growing sugarcane which was 21.25 months of age at time of application in the manner of Example I. The compound was applied at rates of 10, 19, and 38 mgm/stalk which correspond to 1, 2, and 4 lbs/acre, respectively. Trysben was also applied at a rate of 4 lbs/acre. The plants were harvested four weeks after application with the following results:

| Compound | Juice Purity | Pol % Cane |
|---|---|---|
| 9-APE-10.5 (4 lbs/acre) | 79.30 | 10.54 |
| 9-APE-10.5 (2 lbs/acre) | 78.41 | 9.92 |
| 9-APE-10.5 (1 lb/acre) | 62.52 | 5.93 |
| Trysben (4 lbs/acre) | 80.70 | 10.91 |
| Control (untreated) | 64.40 | 6.66 |

This data clearly shows no activity of the 9-APE-10.5 compound at a rate of 1 lb/acre. A rate of 4 lbs/acre is optimal and application at 2 lbs/acre shows signs of decreasing relative to the 4 lbs/acre results.

COMPARATIVE EXAMPLE D

Various materials found to be active in an original screening test (at a rate of 4 lbs/acre) are applied to field growing sugarcane at lower rates including 1 lb/acre and less of active material. More than 3,000 compounds have been tested over an extended period of time and only 2 compounds (one of which is methyl-3,6-dichloro-0-anisate and the other of which is currently chemically unidentified by its supplier) are found to be active at a rate of 1 lb/acre or less. Typical runs are shown below in Table C.

Table C

| Compound | Time of Harvest | | | |
|---|---|---|---|---|
| | Four Weeks After Application | | Five Weeks After Application | |
| | Juice Purity | Pol % Cane | Juice Purity | Pol % Cane |
| 3-carboxy-1-(p-chlorophenyl)-4,6-dimethyl-2-pyridone, Na salt | | | | |
| 19 mg/stalk[1] | 79.48 | 9.98 | 83.99 | 12.52 |
| 9.5 mg/stalk[1] | 77.69 | 9.58 | 72.35 | 8.01 |
| Control | 77.56 | 9.48 | 79.65 | 9.56 |
| Cetyltrimethylammonium bromide | | | | |
| 38 mg/stalk[2] | 81.50 | 9.80 | 86.80 | 11.50 |
| 19 mg/stalk[2] | 77.10 | 8.60 | 73.40 | 7.60 |
| Control | 74.00 | 7.60 | 77.10 | 11.70 |
| 6-azauracil 38 mg/stalk[3] | 70.24 | 8.28 | 77.93 | 10.21 |
| 6-azauracil 19 mg/stalk[3] | 65.34 | 6.20 | 67.48 | 7.15 |
| Control | 59.52 | 5.71 | 67.68 | 6.93 |

[1]Applied to growing sugarcane, 16.5 months of age, at a rate of 19 and 9.5 ml/stalk which corresponds to 2 and 1 lb/acre
[2]Applied to growing sugarcane, 16.0 months of age, at a rate of 38 and 19 ml/stalk which corresponds to 4 and 2 lb/acre.
[3]Applied to growing sugarcane, 16.0 months of age, at a rate of 38 and 19 ml/stalk which corresponds to 4 and 2 lb/acre.

The nature, scope, utility and effectiveness of the present invention have been described and specifically exemplified in the foregoing specification. However, it should be understood that these examples are not intended to be limiting and that the true scope of the invention to be protected is particularly pointed out in the appended claims.

What is claimed is:

1. A process for increasing the sugar yield of field grown, maturing sugarcane which comprises applying to the cane at a time at least about two weeks and up to about twelve weeks prior to harvest as essentially the sole ripening agent in an amount effective to increase sucrose yield, a compound selected from the group consisting of:
   a. linear alcohols containing 11 to 15 carbon atoms,
   b. polyalkylene glycols containing 2 to 3 carbon atoms in the alkylene group, and
   c. ethoxylated phenols or alcohols corresponding to the formula
   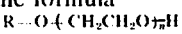
   wherein R is phenyl, alkyl-substituted phenyl wherein the alkyl substituent contains from 8 to 15 carbon atoms, or alkyl of from 8 to 20 carbon atoms, and wherein $n$ is an integer from 6 to 20.

2. A process according to claim 1 wherein the sole ripening agent is a compound selected from the group consisting of ethoxylated phenols or alcohols corresponding to the formula

wherein R is phenyl, alkyl-substituted phenyl wherein the alkyl substituent contains from 8 to 15 carbon atoms, or alkyl of from 8 to 20 carbon atoms, and wherein $n$ is an integer from 6 to 20.

3. A process according to claim 1 wherein the ripening agent is an ethoxylated phenol corresponding to the formula $R+O-CH_2CH_2O)_nH$
wherein R is nonylphenyl and $n$ is 10 to 11.

4. A process according to claim 2 wherein said ripening agent is a composition containing one or more ethoxylated alcohols corresponding to the formula
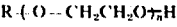
wherein R is alkyl from 8 to 20 carbon atoms and wherein $n$ is an integer from 6 to 20.

5. A process according to claim 4 wherein R is alkyl of from 11 to 15 carbon atoms and mixtures thereof and $n$ is 6.

6. A process according to claim 5 wherein $n$ is 7.

7. A process according to claim 5 wherein $n$ is 9.

8. A process according to claim 5 wherein $n$ is 12.

9. A process according to claim 1 wherein the ripening agent is polyethylene glycol of from about 2000 to about 4000 molecular weight.

10. A process according to claim 1 wherein the compound is applied to the cane in admixture with water as a carrier.

11. A process according to claim 1 wherein the compound is applied in the form of an aqueous solution or suspension at a rate of about 7 to 20 gallons of aqueous composition per acre.

12. A process according to claim 1 wherein the compound is applied in the form of a dust composition.

13. A process according to claim 1 wherein the compound is applied at a rate of at least about 3 lbs/acre.

* * * * *